United States Patent
Batchelor et al.

(10) Patent No.: US 11,413,109 B2
(45) Date of Patent: Aug. 16, 2022

(54) ELECTROSURGICAL INSTRUMENT WITH A FUNCTIONAL ELEMENT

(71) Applicant: GYRUS ACMI, INC., Southborough, MA (US)

(72) Inventors: Kester J. Batchelor, Mound, MN (US); Riyad Moe, Madison, WI (US); Huisun Wang, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 440 days.

(21) Appl. No.: 15/894,212

(22) Filed: Feb. 12, 2018

(65) Prior Publication Data
US 2019/0247141 A1 Aug. 15, 2019

(51) Int. Cl.
*A61B 90/30* (2016.01)
*A61B 18/14* (2006.01)
(Continued)

(52) U.S. Cl.
CPC .......... *A61B 90/30* (2016.02); *A61B 18/1402* (2013.01); *A61B 18/1442* (2013.01); *A61B 2018/0063* (2013.01); *A61B 2018/0091* (2013.01); *A61B 2018/00589* (2013.01); *A61B 2018/00595* (2013.01); *A61B 2018/00601* (2013.01); *A61B 2018/00607* (2013.01); *A61B 2018/1266* (2013.01);
(Continued)

(58) Field of Classification Search
CPC .......... A61B 2018/00053; A61B 2018/00172; A61B 2018/0091; A61B 2018/0231; A61B 2018/1266; A61B 18/14; A61B 18/1402; A61B 18/1442; A61B 90/08; A61B 90/30; A61B 90/36; A61B 2090/309; H02M 7/02
See application file for complete search history.

(56) References Cited

U.S. PATENT DOCUMENTS

| | | | |
|---|---|---|---|
| 2,196,171 A | | 4/1940 | Arnesen |
| 4,856,514 A | * | 8/1989 | Rabinowitz ........ A61B 18/1402 606/37 |

(Continued)

FOREIGN PATENT DOCUMENTS

| | | |
|---|---|---|
| DE | 202004002963 U1 | 4/2004 |
| DE | 102015203617 A1 | 9/2013 |

(Continued)

OTHER PUBLICATIONS

European Extended Search Report for European Application 19156111.7; dated Jul. 17, 2019.
(Continued)

*Primary Examiner* — Ronald Hupczey, Jr.
*Assistant Examiner* — Bradford C. Blaise
(74) *Attorney, Agent, or Firm* — Schwegman Lundberg & Woessner, P.A.

(57) ABSTRACT

An electrosurgical assembly that includes one or more electrodes, and one or more AC conductors electrically connecting the one or more electrodes to a power source that is configured to generate and output an AC power signal to the one or more electrodes via the one or more AC conductors. A rectifier is electrically connected to the one or more AC conductors, and configured to convert the AC power signal into a DC power signal. A light source is electrically powered by the DC power signal.

20 Claims, 7 Drawing Sheets

(51) Int. Cl.
  *H02M 7/06* (2006.01)
  *A61B 18/00* (2006.01)
  *A61B 18/12* (2006.01)
(52) U.S. Cl.
  CPC . *A61B 2018/1412* (2013.01); *A61B 2090/309* (2016.02); *H02M 7/06* (2013.01)

(56) References Cited

U.S. PATENT DOCUMENTS

| | | | |
|---|---|---|---|
| 5,055,100 A * | 10/1991 | Olsen | A61B 18/00 604/22 |
| 5,085,657 A * | 2/1992 | Ben-Simhon | A61M 1/0084 604/35 |
| 5,674,219 A * | 10/1997 | Monson | A61B 18/1402 604/22 |
| 6,325,795 B1 | 12/2001 | Lindemann et al. | |
| 8,506,565 B2 | 8/2013 | DeCarlo | |
| 9,113,891 B2 | 8/2015 | Twomey | |
| 9,375,282 B2 | 6/2016 | Nau, Jr. et al. | |
| 9,554,867 B2 | 1/2017 | Cosmescu | |
| 11,020,166 B2 * | 6/2021 | Batchelor | A61B 18/1206 |
| 2002/0052597 A1 | 5/2002 | Duhaylongsod et al. | |
| 2005/0043594 A1 | 2/2005 | Dinsmoor et al. | |
| 2005/0054993 A1 * | 3/2005 | Falahee | A61M 1/008 604/313 |
| 2006/0291195 A1 * | 12/2006 | Horrell | A61B 90/36 362/109 |
| 2007/0049927 A1 * | 3/2007 | Saltzman | A61B 18/1402 606/45 |
| 2009/0125020 A1 * | 5/2009 | Douglass | A61B 18/1482 606/41 |
| 2010/0280511 A1 | 11/2010 | Rachlin et al. | |
| 2011/0270179 A1 | 11/2011 | Ouyang et al. | |
| 2012/0067212 A1 * | 3/2012 | Warren | A61B 18/00 95/57 |
| 2012/0116369 A1 * | 5/2012 | Viola | A61B 90/30 606/1 |
| 2012/0184951 A1 * | 7/2012 | Viola | A61B 18/1445 606/34 |
| 2012/0283718 A1 | 11/2012 | Cosmescu | |
| 2012/0283728 A1 * | 11/2012 | Cosmescu | A61B 90/35 606/46 |
| 2013/0144281 A1 * | 6/2013 | Lewinsky | A61B 18/20 606/16 |
| 2013/0197317 A1 * | 8/2013 | Daniel | A61B 1/0684 600/249 |
| 2013/0267787 A1 | 10/2013 | Warnock | |
| 2014/0276469 A1 * | 9/2014 | Greep | A61M 1/008 604/264 |
| 2015/0289924 A1 | 10/2015 | Virshek et al. | |
| 2015/0359581 A1 | 12/2015 | Albertal | |
| 2016/0045247 A1 | 2/2016 | Heim et al. | |
| 2017/0086915 A1 | 3/2017 | Batchelor et al. | |
| 2017/0151012 A1 * | 6/2017 | Griffiths | A61B 18/1442 |
| 2019/0178510 A1 * | 6/2019 | Lin | B03C 3/12 |

FOREIGN PATENT DOCUMENTS

| | | |
|---|---|---|
| EP | 2478845 A2 | 7/2012 |
| EP | 3524198 A1 | 8/2019 |
| WO | 2017/031245 A1 | 2/2017 |
| WO | WO-2017053945 A1 * | 3/2017 ............ A61B 18/14 |

OTHER PUBLICATIONS

"European Application Serial No. 19156111.7, Response filed Feb. 13, 2020 to Extended European Search Report dated Jul. 17, 2019", 9 pgs.

* cited by examiner

ELECTROSURGICAL INSTRUMENT WITH A FUNCTIONAL ELEMENT

FIELD

These teachings relate to a medical instrument and a functional element.

BACKGROUND

An electrosurgical medical instrument includes one or more electrodes electrically connected to a power source. The power source is configured to supply a power signal to one or more of the electrodes for electrically effecting an object or anatomical feature with the electrodes.

During a medical procedure, ancillary instruments, such as a light source and/or smoke evacuator, may be used to illuminate a surgical site and/or remove smoke from the surgical site, respectively. These ancillary instruments are typically powered by power sources that are different from the power source that is configured to supply the power signal to the medical instrument and the electrodes.

In addition to energizing the electrodes, it may be desirable to utilize a power signal from the medical instrument power source for other purposes, such as powering ancillary instruments, such as a light source or smoke evacuator. It may also be desirable to combine an electrosurgical medical instrument with one or more ancillary instruments, and power the one or more ancillary instruments with the same power source that is used to power the medical instrument.

SUMMARY

These teachings provide an electrosurgical assembly comprising a medical instrument and an ancillary instrument, which may be referred to herein as a functional element, a DC powered functional element or DC load, an AC powered functional element or DC load, or a combination thereof. The functional element is configured to be powered by the same power source that powers the medical instrument or the one or more electrodes of the medical instrument. According to these teachings, a rectifier is electrically connected to both the power source and the functional element, and the rectifier is configured to convert the AC power signal from the power source into a DC power signal to power the functional element. Advantageously, by combining the medical instrument and the ancillary instrument, the surgical site is decluttered. Moreover, a clinician performing a medical procedure can operate the medical instrument and ancillary instrument with one hand and without relying on another clinician to operate either the medical instrument or the ancillary instrument. Furthermore, operating and instrument costs may be reduced by powering one or more ancillary medical instrument with the same power source configured to power a medical instrument.

These teachings provide an electrosurgical assembly. The electrosurgical assembly comprises a medical instrument and a power source. The power source is configured to supply AC power to the medical instrument to power the medical instrument. A rectifier is electrically connected to the power source. The rectifier is configured to convert the AC power signal from the power source into a DC power signal. The DC power signal is communicated to a functional element that is connected to the medical device to power the functional element. The rectifier can be located in the medical instrument or in the functional element. The functional element may be removably attached to the medical instrument, or integrally attached or formed with the medical instrument. The functional element may be an AC load powered by AC power, or a DC load powered by DC power.

These teachings provide an electrosurgical assembly comprising: one or more electrodes; one or more AC conductors electrically connecting the one or more electrodes to a power source, the power source is configured to generate and output an AC power signal to the one or more electrodes via the one or more AC conductors; a rectifier electrically connected to the one or more AC conductors, and configured to convert the AC power signal into a DC power signal; and a light source that is electrically powered by the DC power signal.

These teachings provide an electrosurgical assembly comprising: a handpiece; one or more electrodes extending from the hand piece; one or more AC conductors electrically connecting the one or more electrodes to a power source, which is configured to generate and output an AC power signal to the one or more electrodes via the one or more AC conductors; a rectifier located inside the hand piece and electrically connected to the one or more AC conductors, and configured to convert the AC power signal into a DC power signal; a pair of electrical terminals located on the hand piece; and a functional element that is removably connected to the hand piece and comprising a housing having a pair of electrical terminals. The pair of terminals on the hand piece are configured to electrically connect to the pair of terminals on the housing of the functional element to communicate the DC power signal to the functional element to power the functional element.

These teachings provide a light comprising: a housing a light source located inside the housing; and a pair of electrical terminals. The pair of electrical terminals are configured to electrically connect to a pair of corresponding electrical terminals located on a medical instrument so that an electrical signal from the medical instrument is provided to the light source to power the light source.

These teachings provide an electrosurgical assembly comprising one or more electrodes; one or more AC conductors electrically connecting the one or more electrodes to a power source that is configured to generate and output an AC power signal to the one or more electrodes via the one or more AC conductors; and a functional element comprising a light source that is electrically powered by the AC power signal.

DETAILED DESCRIPTION

Figure 1A:
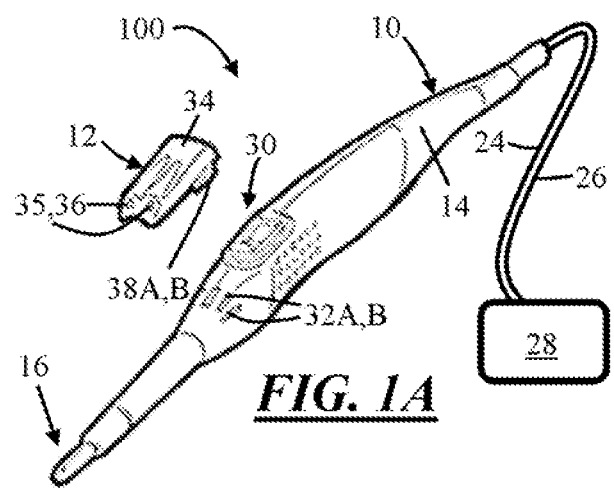
FIG. 1A is a perspective view of an electrosurgical assembly comprising a medical instrument, a power source, and a functional element that is separated from the medical instrument.

These teachings provide an electrosurgical assembly. The electrosurgical assembly may comprise one or more of the elements disclosed herein, including: a medical instrument, an end effector, one or more electrodes, a functional element, a power source, a rectifier, or a combination thereof.

The medical instrument may be any instrument or device for effecting an object or anatomical feature. Effecting may mean, for example, holding, manipulating, engaging, moving, grasping, gripping, constricting, pushing, pulling, cutting, tearing, coagulating, sealing, cauterizing, dissecting, fulgurating, or a combination thereof an object or anatomical feature. The anatomical feature may be any anatomical feature, such as a vessel, tissue, vein, growth, tumor, artery, etc.

The medical instrument can be used in virtually any procedure, whether medically related or not. In medical procedures, the medical instrument can be used in open procedures, laparoscopic procedures, or both.

The medical instrument may be an electrosurgical instrument. The medical instrument may be forceps. The medical instrument may be electrosurgical forceps. The medical instrument may be a pencil or spatula. The medical instrument may be an electrosurgical pencil spatula. The medical instrument may be a debrider or shaver.

The medical instrument is electrically connected to one or more power sources. The power source may be of the type described in U.S. Pat. No. 7,282,048B2, the teachings of which are hereby incorporated by reference herein for all purposes.

The power source may be configured to generate and output or supply an AC power signal to the medical instrument, the one or more electrodes, the rectifier, the functional element, or a combination thereof via one or more conductors or wires (e.g., AC conductors). The one or more AC conductors may be configured to electrically connect the one or more electrodes to a power source so that power from the power source can be transmitted to the one or more electrodes via the one or more AC conductors. The AC power signal from the power source may be an RF output or power signal.

The AC power signal may be provided or passed to the one or more electrodes to activate the electrodes for electrically effecting an object or anatomical feature. For example, the AC power signal provided by the power source to the one or more electrodes may be monopolar energy, bipolar energy, blended energy, or a combination thereof. The AC power signal may include a cut waveform, a coagulation waveform, and/or a blended waveform. During use, an electrical circuit may be completed by passing monopolar energy from the power source to one or more electrodes, to the object or anatomical feature of interest, and to a remote pad or electrode. During use, an electrical circuit may be completed by passing bipolar energy from the power source to an active electrode(s) on the medical instrument, through the object or anatomical feature of interest, and to a return sealing member(s) on the medical instrument.

The medical instrument comprises a hand piece. The hand piece may function to be held by a user. The hand piece may include one or more user controls for operating, actuating, moving, reciprocating, opening, closing, retracting, extending, rotating, turning ON, turning OFF, and/or manipulating the medical instrument, the effector, one or more of the jaws, the jaw assembly, one or more of the electrodes, a cut blade, the functional element, or a combination thereof. The one or more user controls may be adapted to send, transmit, provide, increase, or decrease the AC power signal from the power source to the instrument, the one or more electrodes, the rectifier, the functional element, or a combination thereof. The one or more user controls may be adapted to send, transmit, provide, increase, or decrease the DC power signal from the rectifier to the functional element. The one or more user controls may comprise one or more buttons, levers, triggers, knobs, wheels, or a combination thereof. A user control may also be a foot pedal or other button, lever, trigger, knob, wheel, or a combination thereof that is not part of the immediate hand piece.

The medical instrument, the hand piece, the effector, or a combination thereof may comprise one or more electrical terminals, or two or more electrical terminals. The one or more or two or more electrical terminals that are on the medical instrument, the hand piece, the effector, or a combination may be electrically connected (e.g., a power signal can be communicated to) the rectifier.

The functional element or housing of the functional element may comprise one or more electrical terminals, or two or more electrical terminals that correspond to the electrical terminals on the hand piece. The one or more or two or more electrical terminals that are on the functional element may be electrically connected (e.g., a power signal can be communicated to) the light source, smoke ionizer, etc.

The corresponding electrical terminals may be brought together and may function to electrically connect the hand piece and/or the power source and the functional element. The electrically connected electrical terminals may function to transmit AC power signals and/or DC power signals between the hand piece or power supply and the functional element or the DC load, or the AC load, between the hand piece and the rectifier, or a combination thereof. The electrical terminals may connect with corresponding electrical terminals via a snap fit so that the functional element snaps into the hand piece so that the functional element is retained with the hand piece. Each of the electrical terminals may be in electrical communication with a corresponding AC conductor, DC conductor, or both described herein.

The medical instrument comprises an end effector. The end effector may be configured to perform one or more effecting functions on an anatomical feature. For example, the one or more effecting functions may include: capturing an object or anatomical feature; grasping an object or anatomical feature; providing a clamping force to secure an object or anatomical feature; providing retraction of an object or anatomical feature; providing a compression force across an object or anatomical feature; or a combination thereof. The effector may be used in electrosurgery to perform one or more electrically effecting functions, such as cutting, coagulating, cauterizing, dissecting, and/or fulgurating the object anatomical feature. The end effector may extend from a distal end of the hand piece, and may be manipulated with one or more of the user controls.

The medical instrument or the end effector may comprise a jaw assembly. The jaw assembly may be configured to perform one or more effecting functions discussed above.

The jaw assembly may comprise one or more jaws. One or more of the jaws may be moved relative to one another to move the jaw assembly into a closed configuration and an open configuration by manipulating one or more of the user controls. One or more both the jaws may be, or may comprise, one or more electrodes that are electrically connected to the power source via one or more conductors so that the one or more jaws or the jaw assembly can be used to electrically effect an object or anatomical feature by passing an electrical therapy current to or through the anatomical feature during a medical procedure.

The instrument or end effector may comprise a cut blade. The cut blade may function to cut an object or anatomical feature. The cut blade may be a cutting blade or a scalpel. The cut blade may be or may be connected with an electrode that is electrically connected to the power source via the one or more conductors so that the cut blade can be used to electrically effect an anatomical feature by passing an electrical therapy current to or through the anatomical feature during a medical procedure.

The cut blade may be moved or reciprocated or extended or retracted within the jaw assembly or a blade slot provided therein by moving or manipulating one or more of the user controls. The cut blade can be moved or extended to cut an anatomical feature captured between the jaw assembly when the jaw assembly is in a closed or clamping configuration. The cut blade may cut an anatomical feature after the anatomical feature is clamped and/or coagulated or sealed between the jaws of the jaw assembly.

The end effector, the jaw assembly, or both may comprise one or more electrodes. Each jaw of the jaw assembly may comprise one or more electrodes. The cut blade may comprise one or more electrodes. Each of the electrodes may be in electrical communication with the power source via one or more discrete, corresponding AC conductors or wires so that one or more AC power signal can be provided between the power source and the electrodes. By supplying the one or more electrodes with an AC power signal, the one or more electrodes can be used to electrically effect an anatomical feature during an electrosurgical procedure by cutting, coagulating, cauterizing, dissecting, and/or fulgurating the anatomical feature.

The electrosurgical assembly, the medical instrument, or both comprises one or more functional elements.

The functional element may be an element that is powered by the same power source that is configured to power the medical instrument. The functional element may be an AC load or a DC load that is a target electrical component or powered element that is powered by the power source to produce some function (e.g, a light that turns ON or flashes; a smoke ionizer that gathers, reduces, and/or eliminates smoke particles, etc.). An AC load is a functional element or power element that is powered directly by AC power from the AC power source. A DC load is a functional element or power element that is also powered by AC power from the power source, but the AC power is converted into DC power to power the DC load.

The functional element may be, or may comprise one or more powered elements. A powered element may be one or more lights or a light source, which may be one or more illumination lights, indicator lights, spot lights, LED lights, incandescent lights, halogen lights, fluorescent lights, or a combination thereof that are powered by a DC power signal, a signal from the rectifier, or both. An LED, being a diode, may advantageously provide additional smoothing beyond what the rectifier with the optional filter capacitor can provide, for incrementally improvement of the uniformity of light output. The one or more lights may function to illuminate a surgical site and/or feature of interest.

A powered element may be smoke ionizer or evacuator. The smoke ionizer or evacuator may comprise the teachings disclosed in Applicant's International Application No. PCT/US2016/53717 filed on Sep. 26, 2016, which claims the benefit of U.S. Ser. No. 14/865,420 filed on Sep. 25, 2015, both of which are entirely incorporated by reference herein and form part of this disclosure.

The functional element may removably attached to the medical instrument, the hand piece, the effector, or a combination thereof. Removably attached means that the functional element or the housing can be separated or removed from the medical instrument, the hand piece, the end effector, or a combination thereof without damaging the medical instrument, the hand piece, the effector, the functional element, the housing, or a combination thereof. A removably attached functional element may be advantageous in order to provide a medical instrument that can be individually customized with various functional elements. For example, a removable smoke ionizer or evacuator can be attached to the medical instrument, and then, the smoke ionizer or evacuator can be detached or separated from the medical instrument, and a removable light can be attached to the medical instrument. The medical instrument may also have capability to have two or more functional elements attached to the medical instrument, for example, both a smoke ionizer and a light.

The functional element may be removably connected to the hand piece by way of one or more, or preferably two or more electrical terminals. In addition to connecting the hand piece and the removable component, the electrical terminals may function to send, transmit, or communicate one or more AC power signals, DC power signals, or both between the medical instrument and the functional element.

The functional element may, however, be configured to be permanently attached, or integrally attached to the medical instrument, the hand piece, the end effector, or a combination thereof. Permanently attached means that the functional element or the housing thereof cannot be, or is not intended to be, separated or removed from the medical instrument, the hand piece, the effector, or a combination thereof without damaging the medical instrument, the hand piece, the effector, the functional element, the housing or a combination thereof.

The functional element or the powered element of the functional element may be powered by a DC power signal or an AC power signal. The DC power signal may be supplied by the power source that powers the medical instrument, the electrodes, or both. The DC power signal may be a converted AC power signal from the same power source that is configured to power the medical instrument, the effector, the one or more electrodes, or a combination thereof. The AC power signal may be converted into a DC power signal by one or more rectifiers.

The medical instrument or the functional element may comprise one or more rectifiers. The rectifier may function to convert an AC power signal into a DC power signal. The rectifier may function to convert an AC power signal into a DC power signal; the AC signal may be generated or provided by the power source that is configured to supply a therapy current or power to the one or more electrodes of the medical instrument. The rectifier may convert the AC power signal into a DC power signal by rectifying the AC power signal, and then filtering the power signal. The rectified signal may then be regulated to maintain a constant voltage or current. The rectifier may function to convert or transform an AC power signal from the power source into a DC power signal to turn ON and/or operate the one or more functional elements.

The rectifier may be in electrical communication with one or more AC conductors that are configured to communicate AC power or RF power from the power source to the one or more electrodes. At least some of the AC or RF power intended to be communicated to the one or more electrodes is thus communicated to the rectifier for converting into a DC power signal to power the one or more functional elements. Thus, the rectifier may "piggy back" and/or may be "parasitically attached" to the medical instrument and draw some power from the medical instrument to power the DC powered element.

The DC power signal from the rectifier may be communicated, transmitted or otherwise sent from the rectifier, one or more filter capacitors, or other powered elements of the functional element via one or more conductors or wires (e.g., DC conductors). The one or more DC conductors may be configured to electrically connect the functional element to the rectifier so that power from the rectifier can be transmitted to the removable component via the one or more DC conductors.

The rectifier may be any device or circuit that is configured to convert the AC power signal to the DC power signal for powering the functional element. For example, the rectifier may be a half-wave rectifier or a full-wave rectifier. For example, the full-wave rectifier may be a center-tapped design that uses a transformer with a center-tapped secondary winding and two diodes. For example, the full-wave rectifier may be a full-wave bridge that comprises a plurality of diodes.

The rectifier may comprise one or more Zener diodes, one or more series resistors, or both for voltage regulation after rectification. A Zener diode is a diode that will allow reverse current once a threshold voltage has been surpassed.

The rectifier may be part of, included within, located inside, and/or attached to the medical instrument, the hand piece, the end effector, the functional element, the housing, the power source, or a combination hereof.

The medical instrument, the rectifier, the functional element, the housing, or a combination thereof may comprise one or more electrical connections. An electrical connection may be a point or location on a circuit, an electrical feature or element, or a combination thereof where two or more conductors are electrically connected, coupled or joined. An electrical connection may be a point or location on a circuit, an electrical feature or element, or a combination thereof where the rectifier is connected to the power source, one or more conductors or wires in electrical communication with the power source, or both. An electrical connection may be a point or location on a circuit, an electrical feature or element, or a combination thereof where the functional element is connected to the effector, hand piece, or both. An electrical connection may be a location where two or more conductors are hard-wired together. An electrical connection may comprise a capacitor. An electrical connection may comprise an inductor.

The medical instrument, the rectifier, the functional element, the electrical connection, or a combination thereof may comprise one or more capacitors. The one or more capacitors function to store an electric charge, which may be an AC power signal from the power source. The one or more capacitors may function to create a point of electrical attachment or contact between the rectifier and the power source. That is, one or more conductors may extend from the rectifier to a capacitor, and one or more other conductors may extend from capacitor to the power source.

The one or more capacitors may be smoothing capacitors that function to smooth or even out fluctuations in the AC power signal or the DC power signal. That is, one or more smoothing capacitors may be provided downstream of the power source but upstream of the rectifier to smooth or even out fluctuations in the AC power signal. Additionally, or alternatively, one or more smoothing capacitors may be provided downstream of the rectifier but upstream of the functional element to smooth or even out fluctuations in the DC power signal.

The one or more capacitors may be provided between the AC conductors and/or the DC conductors for EMI filtering to suppress conducted interference that may be present on the corresponding AC conductors or DC conductors.

One or more capacitors may be provided downstream or after the rectifier for filtering of the DC power signal that leaves the rectifier, or to act as a buffer. One or more capacitors may be provided downstream or after the rectifier, but before or upstream of the functional element to stabilize the rectified voltage level from the rectifier by reducing voltage ripple.

The medical instrument, the rectifier, the functional element, the electrical connection, or a combination thereof may comprise one or more inductors. An inductor is an electrical component that stores electrical energy in a magnetic field when electric current flows through it. The one or more inductors may function to create a point of electrical attachment or contact between the rectifier and the power source. That is, one or more conductors may extend from the rectifier to an inductor, and one or more other conductors may extend from inductor to the power source. The inductor may function to smooth or reduce ripple after rectification (i.e., after the AC power signal is converted into a DC power signal) for changing load currents.

Figure 1B:
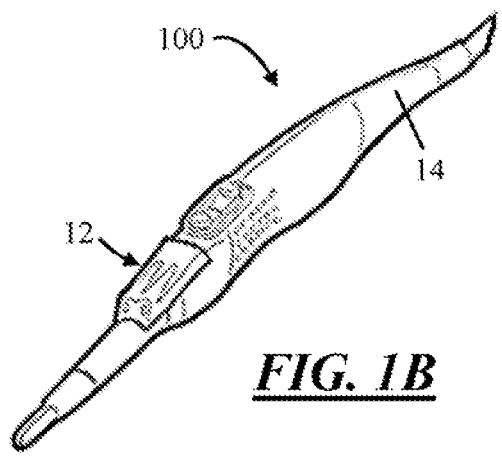
FIG. 1B is a perspective view of the electrosurgical assembly of FIG. 1A with the functional element connected to the medical instrument.

FIGS. 1A and 1B illustrate an electrosurgical assembly 100. The electrosurgical assembly 100 comprises a medical instrument 10 and a functional element 12.

Figure 4:
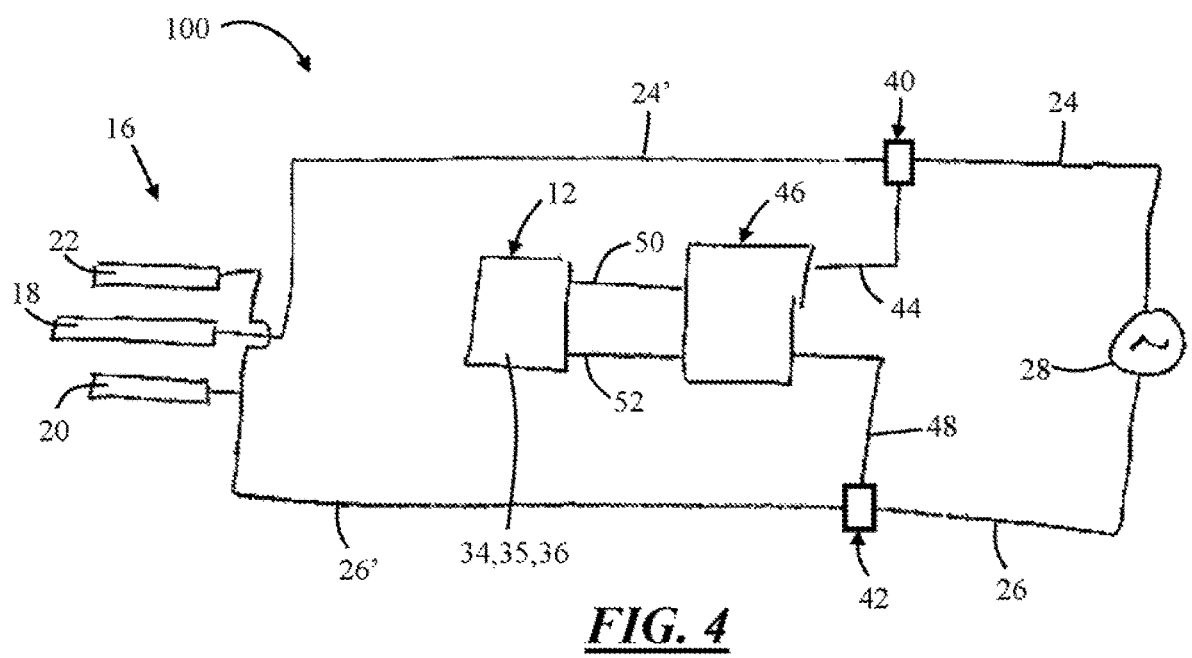
FIG. 4 is an electrical schematic of the electrosurgical assembly.

The medical instrument 10 comprises a hand piece 14 and an end effector 16. The end effector 16 comprises electrodes 18, 20. In some configurations, the end effector 16 comprises electrodes 18, 20, 22 (FIG. 4). One or more of the electrodes 18, 20, 22 may be jaws of a jaw assembly of a forceps device, a cut blade that extends between jaws of a forceps device, or a combination thereof. One or more electrodes 18, 20, 22 may be part of a spatula or pencil.

AC conductors 24, 26 electrically connect the electrodes 18, 20, 22 of the end effector 16 and a power source 28. The power source 28 is adapted to generate and provide an AC power signal to the one or more electrodes 18, 20, 22 via the AC conductors 24, 26.

The medical instrument 10 comprises a user control 30 for activating and/or transmitting the AC power signal from the power source 28 to the medical instrument 10, the one or more electrodes 18, 20, 22, the functional element 12, or a combination thereof; changing an intensity of the AC power signal transmitted from the power source 28, or both. The medical instrument 10 comprises one or more electrical connections or terminals 32A, 32B.

The functional element 12 is adapted to be removably attached to the hand piece 14. The functional element 12 comprises a housing 34. For example, the housing 34 is configured to snap into the hand piece 14. The functional element 12 comprises one or more powered elements 35. The powered elements 35 are lights 36 located inside the housing 34. The functional element 12 or housing 34 comprises one or more electrical connections 38A, 38B or terminals that are adapted to electrically connect with the corresponding electrical connections 32A, 32B on the medical instrument 10 to electrically connect the functional element 12 to the medical instrument 10, as illustrated in FIG. 1B. By way of the electrical connections 32A, 32B and 38A, 38B, an electrical power signal (either an AC power signal or a DC power signal) is communicated from the medical instrument 10, the power source 28, or a rectifier, to the functional element 12 to power the powered elements 35, for example to turn ON the lights 36.

Figure 2:
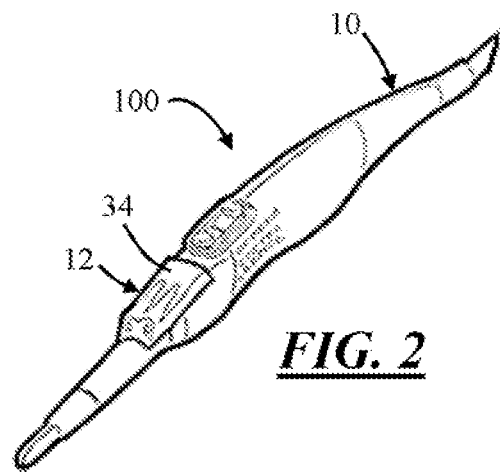
FIG. 2 is a perspective view of an electrosurgical assembly comprising a medical instrument and a functional element that is integral with the medical instrument.

FIG. 2 illustrates an electrosurgical assembly 100, which is substantially similar to the assembly 100 illustrated in FIGS. 1A and 1B, except that the functional element 12 is provided in a housing 34 that is not removable from the medical instrument 10; instead, the functional element 12 and/or housing 34 is permanently attached to, or is integral with the medical instrument 10. In other words, the functional element 12 and/or housing 34 in FIG. 2 is attached to the medical instrument 10 such that the functional element 12 and/or housing 34 cannot be separated or detached from the medical instrument 10 without breaking, damaging, or destroying the medical instrument 10, the functional element 12 and/or housing 34, or a combination thereof.

Figure 3:
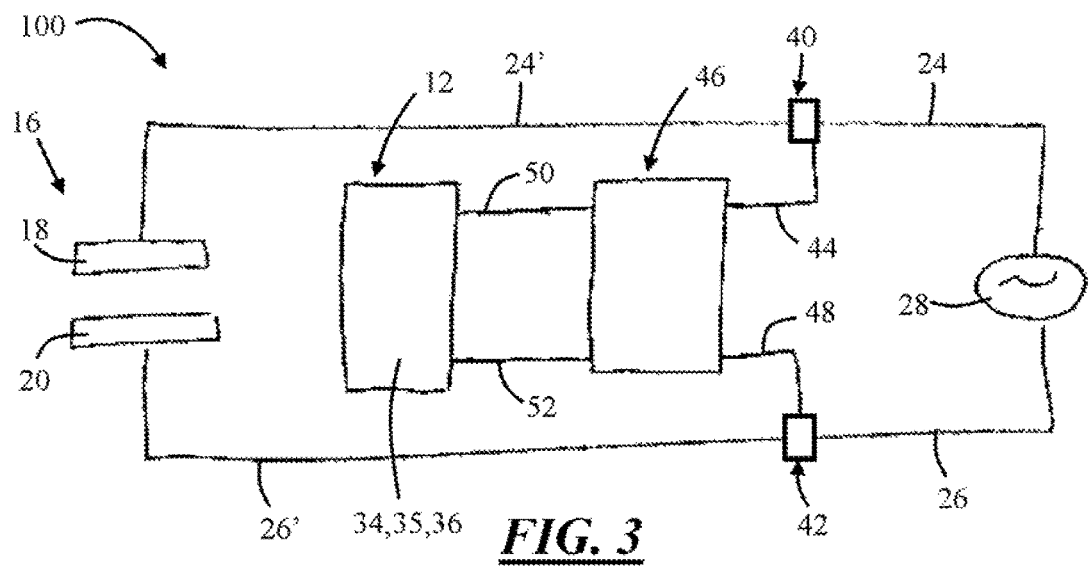
FIG. 3 is an electrical schematic of the electrosurgical assembly.

FIG. 3 is an electrical schematic of the electrosurgical assembly 100. AC conductor 24 extends from a pole of the power source 28, which may be either the active pole or the return pole, to an electrical connection 40. AC conductor 24' extends between and is in electrical communication with the electrical connection 40 and electrode 18 of the end effector 16. AC conductors 24 and 24' may be a single continuous conductor. AC conductor 26 extends from the opposite pole of the power source 28 to an electrical connection 42. AC conductor 26' extends between and is in electrical communication with the electrical connection 42 and electrode 20 of the end effector 16. AC conductors 26 and 26' may be a single continuous conductor. AC power can be provided from the power source 28 to the electrodes 18, 20 via AC conductors 24, 24', 26, 26'. The AC conductors 24, 26 or 24', 24 and 26, 26' may all be contained in a common power cord that plugs into the power source 28 with a single plug having pins corresponding to the conductors 24, 26 or 24', 24 and 26, 26'. Alternatively, AC conductor 24 or 24', 24 may be contained in a first power cord that plugs into the power source 28, and AC conductor 26 or 26', 26 may be contained in a second, discrete power cord that plugs into the power source 28.

AC conductor 44 extends between and is in electrical communication with both of the electrical connection 40 and a rectifier 46. AC conductor 48 extends between and is in electrical communication with both of the electrical connection 42 and the rectifier 46. AC power can be provided from the power source 28 to the rectifier 46 via AC conductors 24, 44, 48, 26.

The rectifier 46 is configured to convert the AC power signal from the power source 28 into DC power signal. DC conductors 50 and 52 extend between and are in electrical communication with the rectifier 46 and the functional element 12 or DC load. The functional element 12 or DC load in FIG. 3 comprises a housing 34 that is permanently attached to or integral with the medical instrument 10, like the one illustrated at FIG. 2. DC power can be provided or transmitted from the rectifier 46 to the functional element 12 or DC load via DC conductors 50 and 52 to power the powered elements 35 with the DC power signal. For example, the lights 36 (FIGS. 1A, 1B, 2) can be powered with the DC power signal from the rectifier 46.

FIG. 4 is an electrical schematic of the electrosurgical assembly 100. AC conductor 24 extends from a pole of the power source 28, which may be either the active pole or the return pole, to an electrical connection 40. AC conductor 24' extends between and is in electrical communication with both of the electrical connection 40 and electrode 18 of the end effector 16. AC conductors 24 and 24' may be a single continuous conductor. AC conductor 26 extends from the opposite pole of the power source 28 to an electrical connection 42. AC conductor 26' extends between and is in electrical communication with both of the electrical connection 42 and electrodes 20 and 22 of the end effector 16. AC conductors 26 and 26' may be a single continuous conductor. AC power can be provided from the power source 28 to the electrodes 18, 20, 22 via AC conductors 24, 24', 26, 26'. The AC conductors 24, 26 or 24', 24 and 26, 26' may all be contained in a common power cord that plugs into the power source 28 with a single plug having pins corresponding to the conductors 24, 26 or 24', 24 and 26, 26'. Alternatively, AC conductor 24 or 24', 24 may be contained in a first power cord that plugs into the power source 28, and AC conductor 26 or 26', 26 may be contained in a second, discrete power cord that plugs into the power source 28.

AC conductor 44 extends between and is in electrical communication with both of the electrical connection 40 and a rectifier 46. AC conductor 48 extends between and is in electrical communication with both of the electrical connection 42 and the rectifier 46. AC power can be provided from the power source 28 to the rectifier 46 via AC conductors 24, 44, 48, 26.

The rectifier 46 is configured to convert the AC power from the power source 28 into DC power. DC conductors 50 and 52 extend between and are in electrical communication with both of the rectifier 46 and the functional element 12 or DC load. The functional element 12 or DC load in FIG. 4 comprises a housing 34 that is permanently attached to or integral with the medical instrument 10, like the one illustrated at FIG. 2, or the housing 34 can be removably attached to the medical instrument 10 like the ones illustrated at FIGS. 1A and 1B. DC power can be provided from the rectifier 46 to the functional element 12 or DC load via DC conductors 50 and 52 to power the powered element 35 with the DC power signal. For example, the lights 36 (FIGS. 1A, 1B, 2) can be powered with the DC power signal from the rectifier 46.

Figure 5:
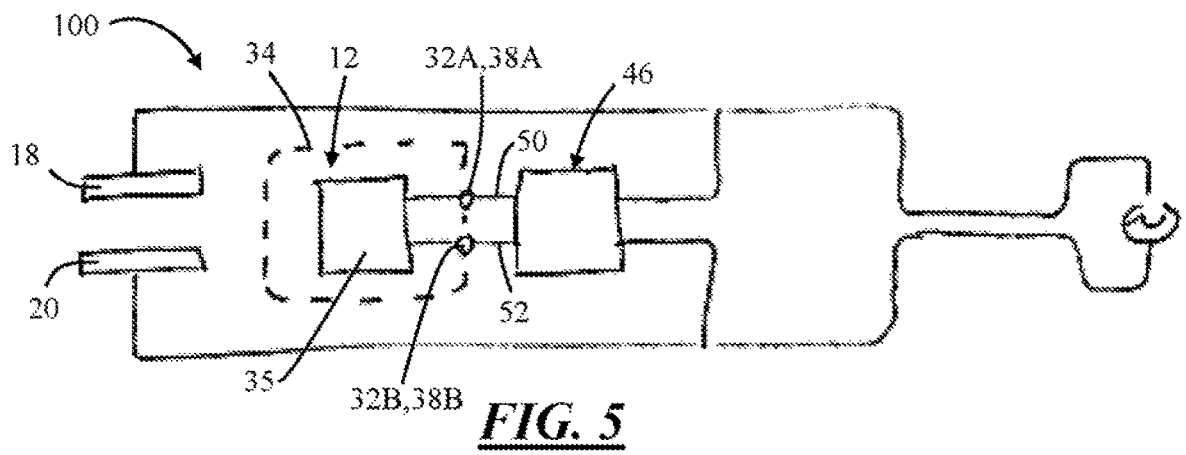
FIG. 5 is an electrical schematic of the electrosurgical assembly.

FIG. 5 is an electrical schematic of the electrosurgical assembly 100, which is substantially similar to the one illustrated and described at FIG. 3. While the electrical schematic of FIG. 5 includes two electrodes 18, 20, the following description of FIG. 5 also applies to an electrosurgical assembly 100 that has three electrodes, like the one illustrated and described at FIG. 4.

The functional element 12 or DC load is configured to be removable or separable from the medical device 10 and/or hand piece 14 without breaking, damaging, or destroying the medical instrument 10, the functional element 12, or both.

That is, referring back to FIGS. 1A and 1B, the housing 34 of the functional element 12 or DC load can be separated from the hand piece 14 and then reconnected. The terminals 38A, 38B on the housing 34 of the functional element 12 or DC load are configured to electrically connect to the terminals 32A, 32B on the hand piece 14, which are in electrical communication with the DC conductors 50, 52 so that DC power from the rectifier 46 can be provided to the functional element 12 when the functional element 12 or DC load is connected to the hand piece 14 to power the powered element 35 inside the housing 34. The terminals 38A, 32B on the housing 34 may snap into the terminals 32A, 32B to electrically connect the functional element 12 and/or the powered element 35 and the hand piece 14.

Figure 6:
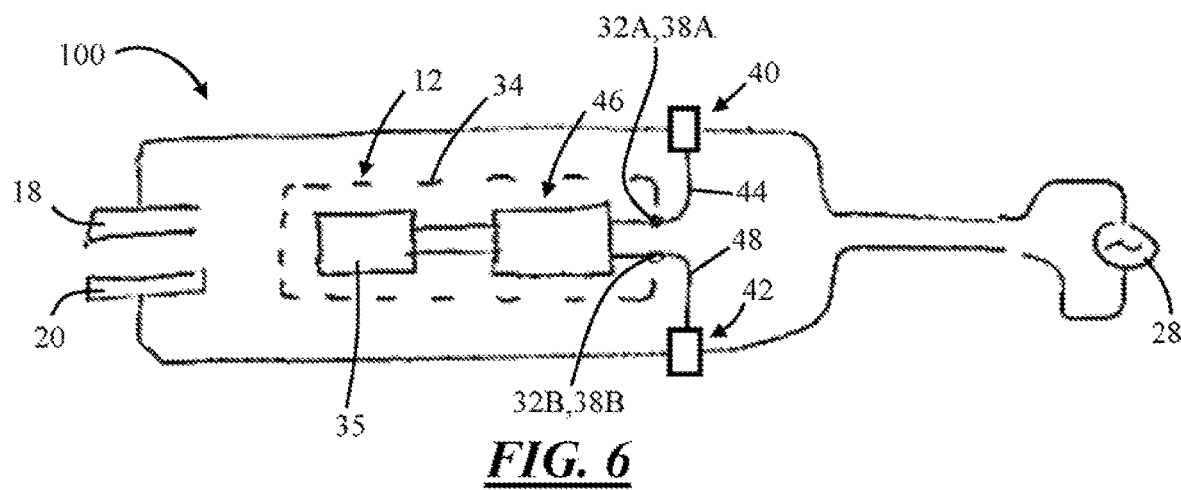
FIG. 6 is an electrical schematic of the electrosurgical assembly.

FIG. 6 is an electrical schematic of the electrosurgical assembly 100, which is substantially similar to the one illustrated and described at FIG. 3. While the electrical schematic of FIG. 6 includes two electrodes 18, 20, the following description of FIG. 6 also applies to an electrosurgical assembly 100 that has three electrodes, like the one illustrated and described at FIG. 4.

The functional element 12 or DC load and the rectifier 46 are both contained in the housing 34. The housing 34 is removable or separable from the medical device 10 and/or hand piece 12 without breaking, damaging, or destroying the medical instrument 10, the functional element 12 or DC load, the rectifier 46, the housing 34, or a combination thereof. That is, referring back to FIGS. 1A and 1B, the housing 34 of the functional element 12 or DC load can be separated from the hand piece 14 and then reconnected without causing any damage thereto. The rectifier 46 may be contained within the housing 34 of the functional element 12 or DC load. The terminals 38A, B on the housing 34 are configured to electrically connect to the terminals 32A, B on the hand piece 14, which are in electrical communication with the AC conductors 44, 48 and/or electrical connections 40, 42 so that AC power from the power source 28 can be provided to the rectifier 46 inside the housing 34 for conversion into DC power for powering the powered element 35 of the functional element 12 or DC load. The terminals 38A, 32B on the housing 34 may snap into the terminals 32A, 32B to electrically connect the functional element 12 or DC load and the hand piece 14.

Figure 7:
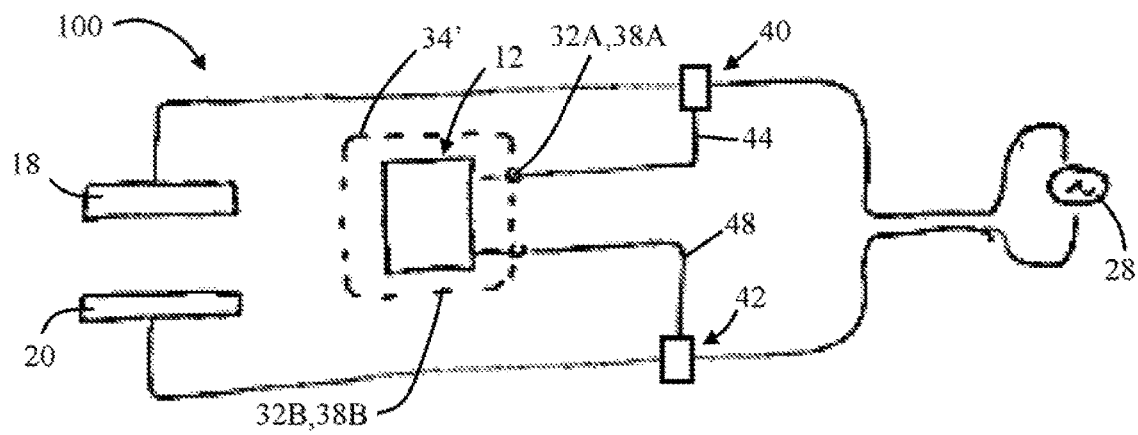
FIG. 7 is an electrical schematic of the electrosurgical assembly.

FIG. 7 is an electrical schematic of the electrosurgical assembly 100, which is substantially similar to the one illustrated and described at FIG. 3. While the electrical schematic of FIG. 7 includes two electrodes 18, 20, the following description of FIG. 7 also applies to an electrosurgical assembly 100 that has three electrodes, like the one illustrated and described at FIG. 4.

The electrosurgical assembly 100 may comprise a functional element 12' or AC load. The functional element 12' or AC load may be substantially similar to the functional elements 12 or DC load described above in the preceding FIGS, but the powered element 35' located inside of the housing 34' of the functional element 12' or AC load in FIG. 7 may be powered by AC power from the power source 28, as opposed to DC power from a rectifier, for example. Accordingly, a rectifier configured to convert AC power from the power source 28 into DC power is not required to power the functional element 12' or AC load. The functional element 12' or AC load may comprise a housing 34' that may be substantially similar to the housing 34 described above. The functional element 12' or AC load and the housing 34' may be removable or separable from the medical device 10 and/or hand piece 12 without breaking, damaging, or destroying the medical instrument 10, the functional element 12', or both. Terminals 38A, 38B on housing 34' are configured to electrically connect to the terminals 32A, 32B on the hand piece 14, which are in electrical communication with the AC conductors 44, 48 and/or electrical connections 40, 42 so that AC power from the power source 28 can be provided to the functional element 12' or AC load to power the powered element 35'.

FIGS. 8-11 illustrate examples of the electrical connections 40, 42 for electrically connecting the rectifier 46 and the power source 28.

Figure 8:
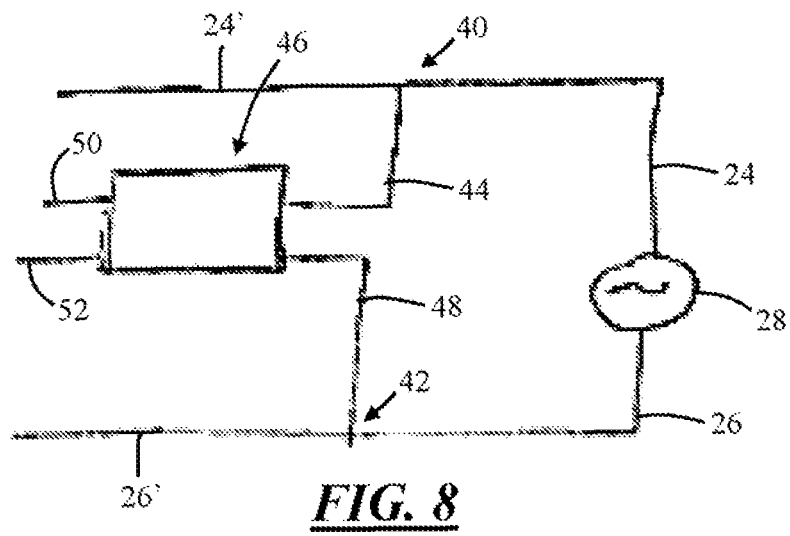
FIG. 8 is an electrical schematic of the rectifier electrically connected to the power source.

In FIG. 8, the AC conductors 44, 48 are directly, electrically connected or hard wired to the corresponding AC conductor 24, 24' and 26, 26' at the corresponding electrical connections 40, 42. Again, AC conductors 24 and 24' may be a common electrical conductor, and AC conductors 26 and 26' may be a common electrical conductor. The AC power from the power source 28 is communicated to the rectifier 46 through the corresponding AC conductors for converting the AC power into DC power. DC conductors 50, 52 extend from the rectifier 46 for communicating DC power to the functional element 12 or DC load (not illustrated).

Figure 9:
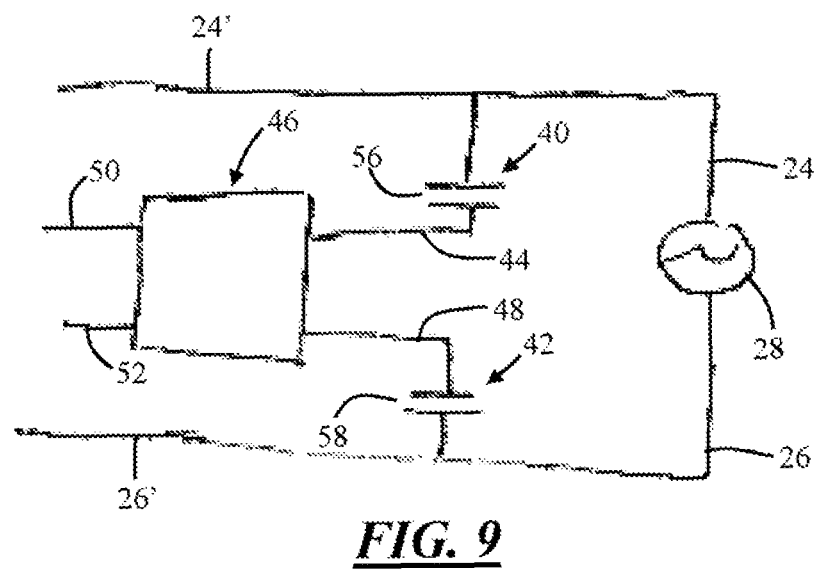
FIG. 9 is an electrical schematic of the rectifier electrically connected to the power source.

In FIG. 9, the electrical connection 40 comprises a capacitor 56. A first side or plate of the capacitor 56 is in electrical communication with AC conductors 24. The opposing second side or plate of capacitor 56 is electrically connected to the rectifier 46 via AC conductor 44.

The other electrical connection 42 comprises a capacitor 58. A first plate of the capacitor 58 is in electrical communication with the AC conductors 26. The opposing second plate of capacitor 58 is electrically connected to the rectifier 46 via AC conductor 48.

AC power from the power source 28 is communicated to the rectifier 46 through the capacitors 56, 58 and the corresponding AC conductors for converting the AC power into DC power. DC conductors 50, 52 extend from the rectifier 46 for communicating DC power to the powered element 35 of the functional element 12 or DC load (not illustrated).

Figure 10:
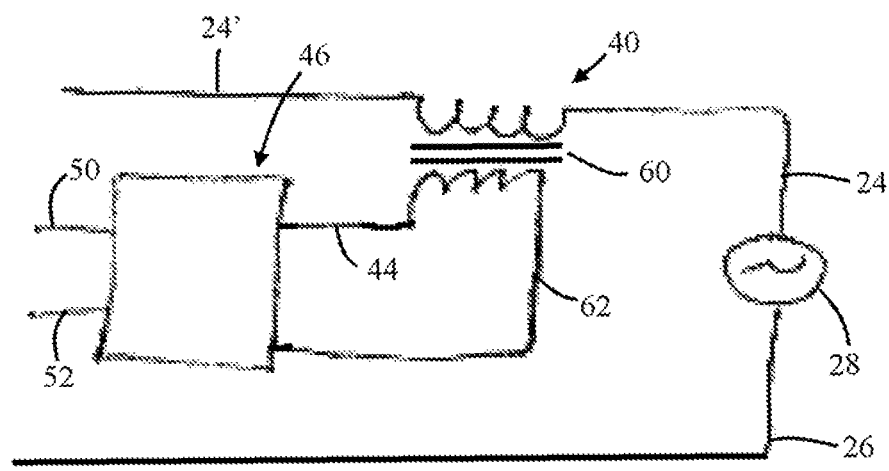
FIG. 10 is an electrical schematic of the rectifier electrically connected to the power source.

In FIG. 10, the electrical connection 40 comprises an inductor 60. A first side of the inductor 60 is in electrical communication with one or both of the AC conductors 24, 24'. Again, AC conductors 24, 24' may be a single conductor electrically connected to the inductor 60. A second side of the rectifier 46 is electrically connected to the rectifier 46 via AC conductors 44 and 62. Inductor 60 does not require connection to the second AC lead 26. Therefore FIG. 10 is an example of a power connection that can be employed in a monopolar electrosurgical device. The AC power from the power source 28 is communicated to the rectifier 46 via the inductor 60 for converting the AC power into DC power. DC conductors 50, 52 extend from the rectifier 46 for communicating DC power to the powered element 35 of the functional element 12 or DC load (not illustrated).

Figure 11:
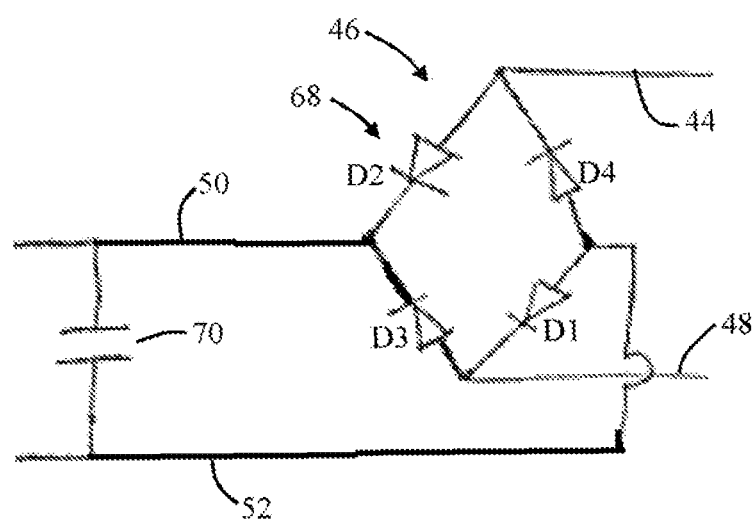
FIG. 11 is an electrical schematic of the rectifier.
Figure 12:
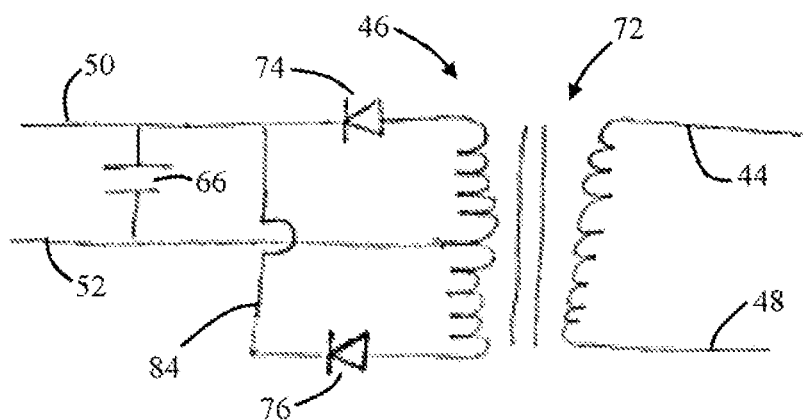
FIG. 12 is an electrical schematic of the rectifier.

FIGS. 11 and 12 illustrate examples of the rectifier 46.

In FIG. 11, the rectifier 46 is a full-wave bridge rectifier 68. The full-wave bridge rectifier 68 comprises diodes D1, D2, D3, D4. AC power signal is supplied to the full-wave bridge rectifier 68 via AC conductors 44 and 48. During the forward phase of the AC signal, AC power signal then travels through diode D2 and exits the full wave bridge rectifier 68 as a DC power signal via DC conductor 50 to the functional element 12 or DC load (not illustrated). The DC power signal then returns to the full-wave bridge rectifier 68 from the functional element 12 or DC load via conductor 52 where the DC power signal moves through diode D1 and then out of the full wave bridge rectifier 68 via conductor 48 to the power source 28 (not illustrated).

During a reverse phase of the AC signal, when the AC signal from the power source 28 reverses, the AC power signal travels through diode D3 and then out of the full wave bridge rectifier 68 as a DC power signal via DC conductor 50 to the functional element 12 or DC load (not illustrated). The DC power signal returns from the functional element 12 or DC load to the full wave bridge rectifier 68 via conductor 52 where the DC power signal moves through diode D4 and then out of the full wave bridge rectifier 68 via conductor 44 to the power source 28 (not illustrated).

A filter capacitor 70 may be optionally provided downstream of the full wave bridge rectifier 64 between the DC conductors 50, 52. The filter capacitor 70 may function to store DC power from the full wave bridge rectifier 68 and then smooth the DC power signal to reduce noise in the DC power signal before the DC power signal is passed to the functional element 12 or DC load. This may help ensure a constant DC power signal is supplied to the powered element 35 of the functional element 12 or DC load to reduce or eliminate flicking of lights 36 in the functional element 12, for element.

In FIG. 12, the rectifier 46 is a full wave rectifier 72. AC power is provided to the full wave rectifier 72 via AC terminals 44, 48. During the forward phase of the AC signal, the AC power signal is directed through diode 74 and then via DC conductor 50 to the functional element 12 or DC load. The DC power signal returns from the functional element 12 or DC load to the full wave rectifier 72 via conductor 52. During the reverse phase of the AC signal, the AC power signal is directed through diode 76 and then via DC conductor 84 to DC conductor 50 and then to the functional element 12 or DC load. The DC power signal returns from the functional element 12 or DC load to the full wave rectifier 72 via conductor 52. The filter capacitor 66 may function to store DC power from full wave rectifier 72 and then smooth the DC power signal to reduce noise in the DC power signal before the DC power signal is passed to the powered element 35 of the functional element 12 or DC load.

Figure 13:
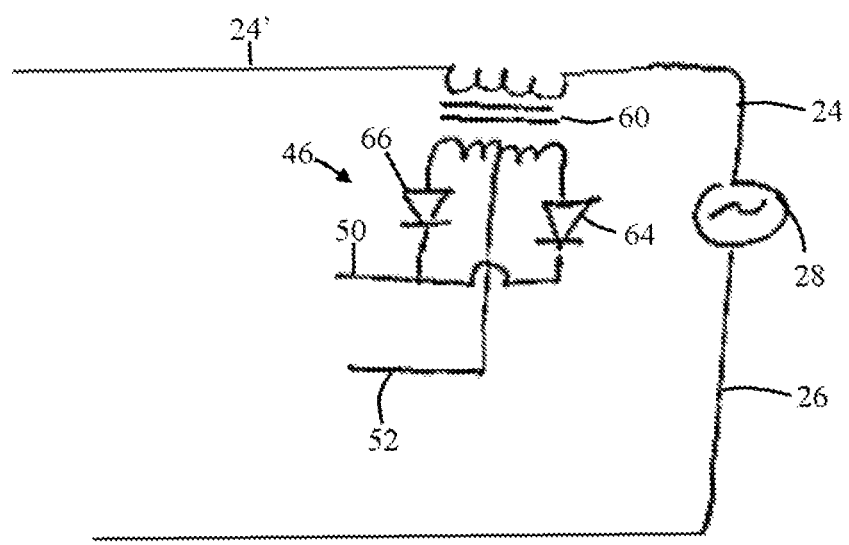
FIG. 13 is an electrical schematic of the rectifier electrically connected to the power source.

In FIG. 13, the electrical connection 40 comprises an inductor 60. A first side of the inductor 60 is in electrical communication with one or both of the AC conductors 24, 24'. Again, AC conductors 24, 24' may be a single conductor. The AC signal is passed from a second side of the inductor 60 to the rectifier 46, which comprises diodes 64, 66. The diodes 64, 66 function to pass the AC signal in a single direction to the DC conductor 50. The DC signal is passed to the functional element 12 (not illustrated) via DC conductors 50, 52.

Figure 14:
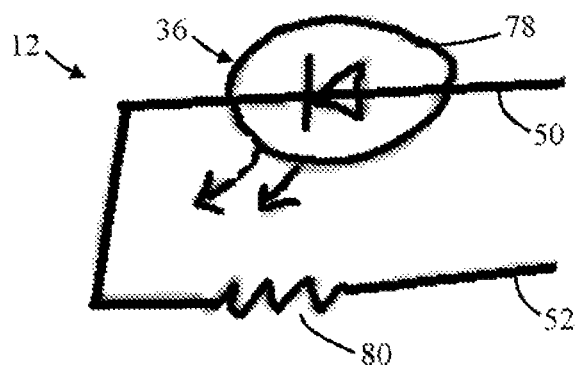
FIG. 14 is an electrical schematic of the functional element.
Figure 15:
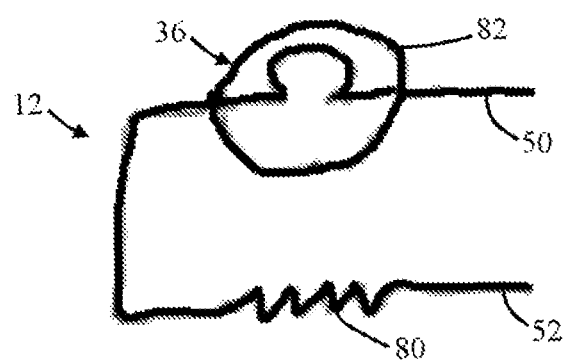
FIG. 15 is an electrical schematic of the functional element.

FIGS. 14 and 15 are electrical schematics of the functional element 12 or DC load. Again, the functional element 12 may be removably attached to the medical instrument 10 or hand piece 14, or the functional element 12 may be permanently or integral with the medical instrument 10 or hand piece 14. While not illustrated in these two Figures, the rectifier 46 may be part of the functional element 12 or contained in the housing 34 of the functional element 12.

In FIG. 14, the functional element 12 or DC load is powered by DC power supplied by the rectifier 46 (not illustrated) via DC conductors 50, 52. The powered element 35 or lights 36 of the functional element 12 may be one or more LED lights 78. The functional element 12 may comprise a capacitor 80.

In FIG. 15, the functional element 12 or DC load is powered by DC power supplied by the rectifier 46 (not illustrated) via DC conductors 50, 52. The powered element 35 or lights 36 of the functional element 12 may be one or more incandescent lights 82. The functional element 12 may comprise a capacitor 80.

The invention claimed is:

1. An electrosurgical assembly comprising:
one or more electrodes;
one or more AC conductors electrically connecting the one or more electrodes to a power source, the power source is configured to generate and output an AC power signal to the one or more electrodes via the one or more AC conductors;
a rectifier electrically connected to the one or more AC conductors, and configured to convert the AC power signal into a DC power signal;
a hand piece including a plurality of electrical terminals;
a light source including a pair of electrical terminals, the light source configured to snap onto the hand piece to removably attach the light source to the hand piece, wherein upon snapping the light source onto the hand piece, the pair of electrical terminals of the light source contacts a pair of the plurality of electrical terminals of the hand piece to electrically power the light source by the DC power signal; and
a smoke ionizer including a pair of electrical terminals and a DC-powered ionizing element including a first DC electrode and a second DC electrode, the smoke ionizer configured to snap onto the hand piece to removably attach the smoke ionizer to the hand piece, wherein upon snapping the smoke ionizer onto the hand piece, the pair of electrical terminals of the smoke ionizer contacts a different pair of the plurality of electrical terminals of the hand piece to electrically power the smoke ionizer by the DC power signal, wherein the smoke ionizer is operable to ionize surgical smoke particles generated at a surgical site using the first DC electrode and to attract the ionized surgical smoke particles towards the second DC electrode for removal from the surgical site.

2. The assembly according to claim 1, wherein the rectifier is located inside the hand piece.

3. The assembly according to claim 2, wherein the plurality of electrical terminals of the hand piece are electrically connected to the rectifier, and
wherein the DC power signal from the rectifier is supplied to the light source through the corresponding pairs of electrical terminals.

4. The assembly according to claim 3, wherein the light source is an LED.

5. The assembly according to claim 1, wherein the rectifier is one of plurality of rectifiers in the electrosurgical assembly.

6. The assembly according to claim 5, wherein the electrical terminals of the hand piece are electrically connected to the one or more AC conductors, and the pair of electrical terminals of the light source are electrically connected to the rectifier via one or more conductors.

7. The assembly according to claim 6, wherein the light source is an LED.

8. The assembly according to claim 1, wherein the rectifier comprises a full wave bridge rectifier.

9. The assembly according to claim 1, wherein the rectifier comprises a full wave rectifier.

10. An electrosurgical assembly comprising:
a hand piece;
one or more electrodes extending from the hand piece;
one or more AC conductors electrically connecting the one or more electrodes to a power source, which is configured to generate and output an AC power signal to the one or more electrodes via the one or more AC conductors;

a rectifier located inside the hand piece and electrically connected to the one or more AC conductors, and configured to convert the AC power signal into a DC power signal;

a pair of electrical terminals located on the hand piece; and a smoke ionizer removably connected to the hand piece via a snap-fit connection between the smoke ionizer and the hand piece, the smoke ionizer comprising a pair of electrical terminals and a DC-powered ionizing element including a first DC electrode and a second DC electrode;

wherein, upon establishing the snap-fit connection between the smoke ionizer and the hand piece, the pair of terminals on the hand piece are configured to electrically connect to the pair of terminals on the smoke ionizer to communicate the DC power signal to the smoke ionizer to power the smoke ionizer; and wherein the smoke ionizer is operable to ionize surgical smoke particles generated at a surgical site using the first DC electrode and to attract the ionized surgical smoke particles towards the second DC electrode for removal from the surgical site.

11. The assembly according to claim 10, wherein the medical instrument is forceps.

12. The assembly according to claim 10, further comprising a light source removably connected to the hand piece via a snap-fit connection between the light source and the hand piece, the light source comprising a pair of electrical terminals configured to electrically connect to a second pair of terminals on the hand piece.

13. An electrosurgical assembly comprising:
one or more electrodes;
one or more AC conductors electrically connecting the one or more electrodes to a power source that is configured to generate and output an AC power signal to the one or more electrodes via the one or more AC conductors;
a rectifier configured to convert the AC power signal into a DC power signal;
a pair of electrical terminals located on a housing portion of the electrosurgical assembly;
a first interchangeable functional element comprising a light source including a pair of electrical terminals, the light source configured to snap onto the housing portion, wherein upon snapping the light source onto the housing portion, the pair of electrical terminals of the light source contacts the pair of electrical terminals of the housing portion to electrically power the light source by the DC power signal; and
a second interchangeable functional element comprising a smoke ionizer including a pair of electrical terminals and a DC-powered ionizing element including a first DC electrode and a second DC electrode, the smoke ionizer configured to snap onto the housing portion, wherein upon snapping the smoke ionizer onto the housing portion, the pair of electrical terminals of the smoke ionizer contacts the pair of electrical terminals of the housing portion to electrically power the smoke ionizer by the DC power signal, wherein the smoke ionizer is operable to ionize surgical smoke particles generated at a surgical site using the first DC electrode and to attract the ionized surgical smoke particles towards the second DC electrode for removal from the surgical site.

14. The electrosurgical assembly according to claim 13, wherein the light source is an LED.

15. The electrosurgical assembly according to claim 13, wherein the rectifier comprises a full wave bridge rectifier.

16. The electrosurgical assembly according to claim 13, wherein the rectifier comprises a full wave rectifier.

17. The electrosurgical assembly according to claim 13, wherein the housing portion comprises a hand piece.

18. The electrosurgical assembly according to claim 13, wherein the rectifier is part of the light source that snaps onto the housing portion.

19. The electrosurgical assembly according to claim 13, wherein the rectifier is located inside the housing portion.

20. The electrosurgical assembly according to claim 13, wherein the rectifier is part of the smoke ionizer that snaps onto the housing portion.

* * * * *